(12) United States Patent
Borody

(10) Patent No.: US 9,468,663 B2
(45) Date of Patent: *Oct. 18, 2016

(54) ENTERIC COMBINATION THERAPY

(71) Applicant: Thomas Julius Borody, Sydney (AU)

(72) Inventor: Thomas Julius Borody, Sydney (AU)

(*) Notice: Subject to any disclaimer, the term of this patent is extended or adjusted under 35 U.S.C. 154(b) by 0 days.

This patent is subject to a terminal disclaimer.

(21) Appl. No.: 14/807,804

(22) Filed: Jul. 23, 2015

(65) Prior Publication Data

US 2015/0328281 A1 Nov. 19, 2015

Related U.S. Application Data

(63) Continuation of application No. 14/324,924, filed on Jul. 7, 2014, now Pat. No. 9,095,545, which is a continuation of application No. 13/499,270, filed as application No. PCT/AU2010/001410 on Oct. 22, 2010, now Pat. No. 8,772,242.

(30) Foreign Application Priority Data

Oct. 26, 2009 (AU) .............................. 2009905229

(51) Int. Cl.
| | |
|---|---|
| A61K 31/485 | (2006.01) |
| A61K 38/14 | (2006.01) |
| A61K 31/4184 | (2006.01) |
| A61K 31/165 | (2006.01) |
| A61K 31/166 | (2006.01) |
| A61K 31/496 | (2006.01) |
| A61K 31/7036 | (2006.01) |
| A61K 31/7048 | (2006.01) |
| A61K 45/06 | (2006.01) |
| A61K 31/4164 | (2006.01) |
| A61K 31/437 | (2006.01) |

(52) U.S. Cl.
CPC ............. *A61K 38/14* (2013.01); *A61K 31/165* (2013.01); *A61K 31/166* (2013.01); *A61K 31/4164* (2013.01); *A61K 31/4184* (2013.01); *A61K 31/437* (2013.01); *A61K 31/485* (2013.01); *A61K 31/496* (2013.01); *A61K 31/7036* (2013.01); *A61K 31/7048* (2013.01); *A61K 45/06* (2013.01)

(58) Field of Classification Search
CPC ........................... A61K 31/485; A61K 38/14
See application file for complete search history.

(56) References Cited

U.S. PATENT DOCUMENTS

| | | | | |
|---|---|---|---|---|
| 6,020,310 A | * | 2/2000 | Beck ..................... | A61K 31/045 424/198.1 |
| 6,413,463 B1 | * | 7/2002 | Yamamoto ........... | A61K 9/4816 264/301 |
| 8,772,242 B2 | * | 7/2014 | Borody .................. | A61K 38/14 514/17.5 |
| 9,095,545 B2 | * | 8/2015 | Borody ................ | A61K 31/165 |
| 2006/0002963 A1 | * | 1/2006 | Rabinovich-Guilatt ................. | A61K 9/1075 424/400 |
| 2007/0110685 A1 | * | 5/2007 | Auspitz ................ | A61K 31/385 424/59 |
| 2011/0064788 A1 | * | 3/2011 | Weimann ............. | A61K 9/7084 424/449 |

FOREIGN PATENT DOCUMENTS

| | | |
|---|---|---|
| JP | 2001524951 | 12/2001 |
| JP | 2005509588 | 4/2005 |
| JP | 2007512336 | 5/2007 |
| WO | 98/43667 | 10/1998 |
| WO | 01/11077 | 2/2001 |

OTHER PUBLICATIONS

Sandler et al. Short-Term Benefit From Oral Vancomycin Treatment of Regressive-Onset Autism. Journal of Child Neurology. Jul. 2000, vol. 15, No. 7, pp. 429-435.*
Borody et al; "Use of high efficacy, lower dose triple therapy to reduce side effects of eradicating helicobacter pylori"; American Journal of Gasteroenterology, Elsevier Science Inc., US, Jan. 1, 1994, v 89, n 1, p. 33-38.

* cited by examiner

*Primary Examiner* — Jeffrey E Russel
(74) *Attorney, Agent, or Firm* — Greer, Burns & Crain, Ltd.; Gregory P. Einhorn

(57) ABSTRACT

There is disclosed herein a composition for treating gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimers Disease, Motor Neurone Disease or autism, the composition comprising: (i) at least two anti-clostridial agents selected from the group consisting of: vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or (ii) at least one anti-clostridial agent selected from the above combined with an opioid blocking agent. There is also disclosed herein a method of treating various gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimers Disease, Motor Neurone Disease or autism, the method comprising administering orally, via enema or by suppository: (i) a composition of the invention; (ii) at least two anti-clostridial agents selected from the group consisting of: vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or (iii) at least one anti-clostridial agent selected from the above and an opioid blocking agent to a patient in need of such treatment.

15 Claims, No Drawings

ENTERIC COMBINATION THERAPY

This application is a continuation of U.S. patent application Ser. No. 14/324,924, filed Jul. 7, 2014 (now pending), which is a continuation of U.S. patent application Ser. No. 13/499,270, filed Apr. 25, 2012, now U.S. Pat. No. 8,772,242, issued Jul. 8 2014, which is a national phase patent utility filing under 35 USC §371, for International (PCT) Patent Application serial No. PCT/AU2010/001410, filed Oct. 22, 2010, which claims benefit of priority to Australian Patent Application Serial No. 2009905229, filed Oct. 26, 2009. The aforementioned applications are expressly incorporated by reference herein in their entirety for all purposes.

TECHNICAL FIELD

The present invention relates generally to the field of pharmaceutical compositions. More specifically the present invention relates to the pharmaceutical composition for treating gastrointestinal disorders and uses thereof.

BACKGROUND OF THE INVENTION

Bowel Flora

The human bowel flora is complex and is composed of around 24,000 bacterial subspecies. It is considered to be a 'virtual organ' and is poorly understood because no more than approximately 15%-20% of the bacterial types have ever been cultured. Indeed, there is a real need among medical practitioners to better understand the concept of bowel flora being a 'virtual organ' which is abnormal or infected for example. Bowel flora can be infected either as an acute infection where the infecting agent can be bacteria, viruses or parasites. The flora can also be infected for a prolonged period i.e. a chronic infection e.g. *C. difficile, Giardia lamblia, Giardia Blastocystis hominis, Aeromonas* or other pathogens. In this invention the concept of a chronic bowel flora infection will be expanded and addressed. It should also be noted that in spite of knowing some acute and chronic infective agents the overwhelming majority of agents infecting the bowel flora are yet to be described and discovered.

Constipation

Constipation according to the view taken in this Patent Application is one such infective disorder of the virtual organ—the bowel flora. It is considered to be an infection by a bacterium or bacterial species capable of producing bioactive substances which affect the bowel wall and the body in general. In contrast to the present view of this inventor, many theories have been put forward as to the cause of constipation. In the past numerous publications have avoided dealing with a cause of constipation and addressed associations rather than causality. Causality has at times been discussed but has been ascribed to differences in diet, psychological causes, motility disturbances, enteric nervous dysplasia and others. Although there are many secondary causes of constipation such as hypothyroidism and various medications, the most common cause of constipation remains obscure. Indeed, patients and doctors remain baffled by the fact that the common variety everyday constipated patient generally eats an average amount or an excessive amount of fibre, drinks enough water and has an average exercise programme—and yet remains constipated—sometimes for days on end. It is also known that taking fibre away from normal people does not cause them to be constipated. Hence, there is a discrepancy between our ideas or beliefs and the real cause of constipation.

Looking at past therapies, constipation has been treated by methods which have often been found by chance, trial and error, or as a side effect of a novel therapy. Mild constipation will respond to change in diet, increase in fibre intake and various laxatives including senna, coloxyl, teas and osmotic laxatives such as lactulose, sorbitol, mannitol and PEG 3550. Various other laxatives have been described including colchicine, bisacodyl, castor oil, linactolide and prucalopride. Methyl naltrexone and naloxone have also been used in opiate-induced constipation. Probiotics have been used empirically and serotonin receptor agonists including tagaserod have been used. Cisapride, metoclopromide, mosapride and domperidone have been shown to increase motility in some patients.

However, no current literature refers to constipation as being a possible infection of gut flora with a particular set of bacterial agents that would be mediating constipation via bioactive substances produced by these bacteria. Although some antibiotics have been listed in literature as affecting bowel activity when used in constipation including neomycin, clarithromycin, metronidazole and rifaximin the results have been variable and not reproducible [Brandt L J et al *Amer Journal Gast* 2009; 104(Suppl): S8-S35.]

Overall then, previous and current medications being developed for the treatment of constipation appear to be dealing with mechanisms that do not address the underlying mechanism of constipation as described in this patent application. Furthermore, some systemic and neurologic conditions are associated with constipation and other bowel disorders which in part may be causally related, for example Parkinsons disease, MS, Alzheimers Disease, Motor Neurone Disease [also known as ALS], autism and other neurologic disorders.

OBJECT OF THE INVENTION

It is an object of the present invention to overcome or substantially ameliorate at least one of the above disadvantages or to provide a suitable alternative.

SUMMARY OF THE INVENTION

According to a first aspect of the present invention there is provided a composition for treating gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimer's Disease, Motor Neuron Disease or autism, the composition comprising:

(i) at least two anti-clostridial agents selected from the group consisting of:

vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or (ii) at least one anti-clostridial agent selected from the above combined with an opioid blocking agent.

According to a second aspect of the present invention, there is provided a method of treating various gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimer's Disease, Motor Neuron Disease or autism, the method comprising administering orally, via enema or by suppository:

(i) a composition of the invention;

(ii) at least two anti-clostridial agents selected from the group consisting of:

vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or (iii) at least one anti-clostridial agent selected from the above and an opioid blocking agent to a patient in need of such treatment.

In one embodiment, the agents are administered simultaneously or consecutively in any order.

According to a third aspect of the present invention there is provided use of:

(i) at least two anti-clostridial agents selected from the group consisting of:

vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or (ii) at least one anti-clostridial agent selected from the above combined with an opioid blocking agent in the manufacture of a medicament for treating various gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimer's Disease, Motor Neuron Disease or autism.

According to a fourth aspect of the present invention there is provided use of at at least one anti-clostridial agent selected from the group consisting of:

vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid;

combined with an antiopioid blocking agent in opioid-induced constipation.

DEFINITIONS

The following definitions are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

All the references cited in this application are specifically incorporated by reference are incorporated herein in their entirety. Inclusion herein of any given reference is not intended to indicate that the reference is generally known in Australia or elsewhere.

DETAILED DESCRIPTION OF THE PREFERRED EMBODIMENTS

There is disclosed herein a composition for treating gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimer's Disease, Motor Neuron Disease or autism, the composition comprising (i) at least two anti-clostridial agents selected from the group consisting of:

vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or (ii) at least one anti-clostridial agent selected from the above combined with an opioid blocking agent.

As required, the composition may include a pharmaceutically acceptable carrier.

In one embodiment the vancomycin derivative is carbohydrate-modified vancomycin, vancomycin-disulfide derivative, lipidated vancomycin, chlorobiphenyl-desleucyl-vancomycin, oritavancin, telavancin, or chlorobiphenyl vancomycin.

In one embodiment the aminoglycoside is selected from the group consisting of streptomycin, neomycin, framycetin, paromomycin, ribostamycin, kanamycin, amikacin, arbekacin, beanamycin, dibekacin, tobramycin, spectinomycin, hygromycin B, paromomycin sulfate, streptomycin, gentamicin, netilmicin, sisomicin, isepamicin, verdamicin, astromicin and mixtures thereof.

In one embodiment the nitroimidazole is selected from the group consisting of metronidazole, tinidazole, nimorazole, secnidazole, ordinazole and mixtures thereof.

In one embodiment the ansamycin is selected from the group consisting of rifaximin, rifampicin, rifabutin, rifapentine and mixtures thereof.

In one embodiment the prokinetic agents are selected from the group consisting of tegaserod, domperidone, metoclopramide, mosapride, erythromycin and mixtures thereof.

In one embodiment the 5-aminosalicylic acid is selected from mesalazine, olsalazine, balsalazide and mixtures thereof.

In one embodiment the antiopioid blocking agent is selected from methyl naltrexone or naloxone hydrochloride.

In one embodiment the composition includes the combination of vancomycin and metronidazole.

In another embodiment the composition includes the combination of vancomycin and rifaximin.

In one embodiment the composition includes the combination of rifaximin and prucalopride.

In one embodiment the composition includes the combination rifaximin, metronidazole and colchicine.

In one embodiment the composition includes the combination vancomycin, metronidazole and colchicine.

In one embodiment the composition incudes the combination vancomycin, aminoglycoside and colchicine.

In one embodiment the composition includes the combination rifamycin, colchicine and metronidazole.

In one embodiment the composition includes the combination vancomycin together with a prokinetic agent.

In one embodiment the composition includes the combination vancomycin, olsalazine and colchicine.

In one embodiment the composition includes the combination of vancomycin and methyl naltrexone or naloxone hydrochloride.

In one embodiment the composition includes the combination of naloxone hydrochloride, vancomycin and metronidazole.

In on embodiment the composition includes the combination of naloxone hydrochloride and colchicines.

In one embodiment the composition includes the combination of naloxone hydrochloride, vancomycin, and rifaximin.

In one embodiment the composition includes the use of naloxone hydrochloride and rifaximin.

In another embodiment, the present invention relates to a method of treating various gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy flatulence, halitosis, chronic fatigue, bloating, proctalgia fugax, Parkinsons disease MS, Alzheimer's Disease, Motor Neuron Disease or autism, the method comprising administering orally, via enema or by suppository;
(i) a composition of the invention;
(ii) at least two anti-clostridial agents selected from the group consisting of:
vancomycin, vancomycin derivatives, a multi-valent polymer of vancomycin, aminoglycosides, nitroimidazoles, ansamysins, nifuroxazide, colchicine, prucalopride, prokinetic agent and 5-aminosalicylic acid; or
iii) at least one anti-clostridial agent selected from the above and an opiod blocking agent to a patient in need of such treatment.

In one embodiment the agent is administered in doses ranging from 50 mg per day to 500 mg per day.

In one embodiment when present, the colchicine is administered in doses of 0.005 mg to 5 mg per day and the 5-aminosalicylic acid is administered in doses of 100 mg to 3 gm per day.

In various embodiments, the agents are administered simultaneously such as in the form of a single composition of the invention or are administered separately in any order. In various embodiments, the agents administered may be those listed above as combinations. For example, the combination of vancomycin and metronidazole; the combination of vancomycin and rifaximin; the combination of rifaximin and prucalopride; the combination rifaximin, metronidazole and colchicine; the combination vancomycin, metronidazole and colchicine; the combination vancomycin, aminoglycoside and colchicine; the combination rifamycin, colchicine and metronidazole; the combination vancomycin together with a prokinetic agent; the combination vancomycin, olsalazine and colchicine; the combination of vancomycin and methyl naltrexone or naloxone hydrochloride, the combination of naloxone hydrochloride, vancomycin and metronidazole; the combination of naloxone hydrochloride and colchicines; the combination of naloxone hydrochloride, vancomycin, and rifaximin; or the combination of naloxone hydrochloride and rifaximin.

In another embodiment, the present invention relates to use of:
(i) at least two anti-clostridial agents selected from the group consisting of:
vancomycin, vancomycin derivatives, a multi-valent polymer of vancomycin, aminoglycosides, nitromidazoles, ansamysins, nifuroxazide, colchicine, prucalopride, prokinetic agent and 5-aminosalicylic acid; or
(ii) at least one anti-clostridial agent selected from the above combined with an opioid blocking agent.
in the manufacture of a medicament for treating various gastrointestinal or neurological disorders, constipation, functional constipation, irritable bowel syndrome, diverticulitis, travelers diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating, proctalgia fugax, Parkinsons disease, MS, Alzheimer's Disease, Motor Neuron Disease or autism.

The description of the invention is tied to the description of the casuality. Mentioned above is the concept of the bowel flora being a virtual organ, consisting largely of various bacteria most of which are not known to mankind. A number of clinical observations have led the inventor to this conceptualisation of the mechanisms which have led to the invention. Firstly when patients with constipation take multiple antibiotics e.g. for treatment of *Helicobacter pylori* infection, it was noticed their constipation resolves and remains much better for several days even after they stop the antibiotics, suggestine that constipation is mediated by an infection of the bowel flora which was suppressed by the antibiotics. Furthermore, the use of vancomycin alone has been previously described in constipation and these points to constipation being caused by a Clostridial infection (Andrews et al *Euro J Gast Hep* 1992; 4:245-7, and Celik A F et al, *Alimentary Pharmacol and Ther*, 1995; 9:63-68). However, the inventor recognised that the use of vancomycin alone is inefficient and requires an improvement because not all patients respond and respond but partially to be clinically effective. Nevertheless, such an observation has strongly pointed to bowel flora abnormality or bowel flora infection as the primary cause of most cases idiopathic constipation. The inventor's belief that the etiology of constipation being infection was further strengthened by the use of 'faecal bacteriotherapy' i.e., when transplantation of bowel flora was shown to reverse constipation (T J Borody et al *J Clin Gastroenterol* 2004; 38:475-483). The implantation of new bacteria from a healthy donor has been definitively shown to produce prolonged reversal of constipation in the occasional patients treated (Andrews P J et al *European Gastroenterology and Hepatology* 1992; 4:245-247).

Hence the mechanism of the abnormality appears to be an infective one and probably similar to that of *Clostridium Botulinum* which also causes severe constipation as one of its first symptoms in babies infected with this agent. It is likely that such Clostridia release neuro-active opioid-like substances which then paralyse the bowel's motor activity

[peristalsis] which is in effect, the mechanism for constipation in most patients. Such bacterial substances enter the circulation and may also paralyse the small bowel, so causing accumulation of gas in the small bowel which clinically presents as bloating. Such circulating substances are likely also to reduce gastric emptying by partial paralysis [slow gastric emptying] and by relaxing the tone of the lower oesophageal sphincter causing reflux oesophagitis—the mechanism of oeosophagitis known to be frequently associated with constipation. Blockade of these neuro-active opioid-like substances by their antagonists would be therefore expected to further help resolve the dysmotility of the colon, small bowel, stomach and oesophagus. These would include methyl naltrexone and naloxone hydrochloride in doses ranging from 0.01 mg to 1000 mg per day.

Hence, the appropriate approach to the treatment of constipation would be to treat the causal infective agent or agents, even though they may not be able to be cultured and block the opioid neoropeptides they secrete.

Given the background given above and the results from the treatment of numerous patients, the invention constitutes an antimicrobial combination therapy that would pass down the bowel and suppress or eradicate the culprit infective agent or agents and in some circumstances opioid blockers to make the treatment more effective. Various agents are capable of inhibiting Clostridia and cause laxation. The foremost of these is vancomycin or vancomycin derivative when used orally as it is mostly not absorbed by the gut. The antimicrobial agents include vancomycin, a multi-valent polymer of vancomycin, aminoglycosides including streptomycin, neomycin, framycetin, paromomycin, ribostamycin, kanamycin, amikacin, arbekacin, beanamycin, dibekacin, tobramycin, spectinomycin, hygromycin B, paromomycin sulfate, streptomycin, gentamicin, netilmicin, sisomicin, isepamicin, verdamicin and astromicin. Other anti-infective agents that can be used include nitroimidazoles such as metronidazole, tinidazole, nimorazole, secnidazole and ordinazole. Another group of agents that is active is rifaximin, a semi synthetic rifamicin based agent from a larger family of Ansamycin's which includes rifampicin and rifabutin as well as rifapentine. Rifaximin is preferable because it is not absorbed from the intestine. Another useful agent to be in combination with those mentioned includes nifuroxazide—another non-absorbed product. Various medications which can increase water secretion in the bowel such as colchicine and prucalopride can also be effectively combined. Opioid blocking agents include methyl naltrexone and naloxone hydrochloride.

The pharmacological combinations that have been found to be useful include a composition of two or more anti-clostridial alone or anti-clostridial agents combined with other medications enumerated. The invention describes compositions and use thereof for the manufacture of a medication for the treatment of constipation and constipation-associated conditions. The best disclosed compositions include that of vancomycin and metronidazole, vancomycin and rifaximin, vancomycin and naloxone hydrochloride and rifaximin and naloxone hydrochloride. These can be taken orally in doses of these medications ranging from 0.01 mg per day through to 5000 mg per day. The combination can be taken as the currently available capsules and tablets in single or divided dosing regimens. Another and preferable combination is that of a capsule or tablet which is enteric coated so that it opens in the distal small bowel or the large bowel so reducing any absorption of absorbable drugs e.g. metronidazole. The medication can be taken long term to suppress the Clostridial super-infection of the bowel flora which so helps to increase gut motility. Other combinations include rifaximin and prucalopride in same covered dose ranges in single or divided doses, rifaximin, metronidazole and colchicine, and vancomycin, metronidazole and colchicine—colchicine in doses of 0.005 mg-5 mg per day. This combination can also be as an enteric-coated product to limit absorption. A combination of vancomycin, aminoglycosides and colchicine is yet another composition. Rifamycin, colchicine and metronidazole is yet another combination.

A further set of agents which can be added to single antibiotics or combined antibiotics include prokinetic agents such as tegaserod, domperidone, metoclopramide, mosapride, eythromycin and 5-aminosalicylic acid products which also inhibit Clostridia including mesalazine, olsalazine and balsalazide. In respect to these, one could combine vancomycin with olsalazine—the latter 100 mg—3 gm per day, or vancomycin with any other prokinetic agent used in accepted appropriate doses. In a further combination the use of vancomycin, olsalazine and colchicine can be combined. In fact any of the groups above can be combined in two or more combinations to control the constipation of bacterial infection.

Apart from describing the various compositions useful in the treatment of various gastrointestinal disorders, it should be mentioned that a number of often disparate disorders have been noticed to respond well to these combinations, indicating a microbiologic etiology of such disorders. These include constipation, functional constipation, irritable bowel syndrome, diverticulitis, traveler's diarrhoea, chronic idiopathic nausea, IBD-associated constipation and diarrhoea, pseudo-obstruction, diabetic gastroparesis, cyclic vomiting, reflux oesophagitis, autism enteropathy, flatulence, halitosis, chronic fatigue, bloating and proctalgia fugax and in the above neurological disorders.

The invention will now be described with reference to the following examples which should not be construed as limiting on the invention.

EXAMPLES

Example 1

A 38 year old female patient with life-long constipation, defecating between 0-2 times per week, had multiple investigations carried out and no abnormalities were found with respect to the colon or the bowel flora, and had failed known standard therapies. She was not hypothyroid and had otherwise normal blood tests. She was given a trial of Vancomycin 500 mg bd and Metronidazole 200 mg bd and began defecating by day 3 of the treatment. She was able to continue defecating normally with her constipation completely being reversed while she took the therapy for 4 weeks. After stopping the therapy, within 2 weeks the constipation started recurring. Restarting the treatment again allowed her to defecate normally. Apart from the constipation her bloating was markedly reduced during treatment, and her sensation of 'fullness' was improved and her reflux symptoms also lessened. Her previous tiredness was markedly reduced during treatment.

Example 2

An elderly gentleman with severe constipation requiring 6 coloxyl tablets per day and Parkinson's disease was commenced on Vancomycin 500 mg bd, Metronidazole 400 mg bd and Colchicine 0.5 mg bd. Within 3 days he was defecating normally and was able to stop taking the Coloxyl.

Unexpectedly, by week 4 his Parkinson's disease had improved quite dramatically. In spite of still-continuing to take Sinemet in his original dose, he no longer experiences any tremor and over the period of several months his gait improved and 'Glabellar tap' test reversed to normality. Continuing the treatment for over a year—his constipation remained completely gone, his Parkinson's was virtually undetectable and he was able to reduce his dose of Sinemet, suggesting his Parkinson's disease neurotoxicity may have originated from the bowel flora.

Example 3

A 41 year old female with a 10 year constipation history associated bloating, tiredness and headaches was commenced on 500 mg of Vancomycin twice daily and Rifaximin 200mg twice daily. After a week's treatment her constipation improved markedly but the Rifaximin had to be increased to 400 mg twice daily for the constipation and other symptoms to be virtually completely undetectable. Progressively her bloating improved and her tiredness and headaches improved. She continued on treatment now for over 3 months and continues well on the therapy not wanting to stop the treatment because she feels so well.

Example 4

An 8 year old male with constipation alternating at times with diarrhea with Autism Spectrum Disorder was commenced on Vancomycin 250 mg twice daily together with Naloxone hydrochloride 10 mg twice daily. After 3 weeks of treatment the constipation was completely resolved but in addition his behavior and lethargy changed. He became affectionate and relatively calm, achieving toilet retraining which he had never previously achieved. His vocabulary began to increase quite rapidly, his on task performance, compliance with parental requests and awareness of surroundings improved quite quickly and he was engaging in positive activities. Repetitive and self stimulatory behaviors were reduced. The improvement lasted for the duration of four months treatment as various parameters kept on improving.

Example 5

Elderly male with severe constipation, bloating and abdominal pain and early Parkinson's disease characterized by stiffness was commenced on Vancomycin 500 mg twice daily together with Rifaximin 500 mg twice daily and Naloxone hydrochloride 10 mg twice daily. Within a week he was defecating normally. I was able to stop the various teas and Normacol together with Movicol which he was using for constipation. By week 6 his stiffness had markedly improved, he had stopped "freezing" while attempting to initiate walking and his fine tremor, previously present, was no longer detectable. Cogwheel rigidity also improved and he was able to reduce his anti-Parkinsonian treatment by about 30% at this stage. He continued the treatment for 6 months and his Parkinsonian symptoms further regressed although they were not completely undetectable at this stage.

Example 6

A 52 year old female with lifelong constipation associated with marked bloating was commenced on 500 mg Vancomycin twice daily, 500 mg Rifaximin twice daily and Naloxone hydrochloride 10 mg twice daily. After one week of treatment her constipation improved markedly and kept on improving over the next 2-3 weeks. Her bloating took some time to resolve and about 5 weeks she was not able to detect bloating even though she may have eaten a fatty meal. She continued on therapy for 6 months without changing and she was asymptomatic at that time.

Although the invention has been described with reference to specific examples, it will be appreciated to those skilled in the art that the invention may be embodiment in many other forms.

The invention claimed is:

1. A method of treating or substantially ameliorating diarrhea with autism spectrum disorder, or autism enteropathy, the method comprising administering
at least one anti-clostridial agent and at least one opioid blocking agent, to a patient in need of such treatment.

2. The method of claim 1 wherein the at least one anti-clostridial agent or the at least one opioid blocking agent is administered in doses ranging from 0.01 mg per day to about 5000 mg per day.

3. The method of claim 1, wherein the at least one anti-clostridial agent or the at least one opioid blocking agent is administered orally, via enema or by suppository.

4. The method of claim 1, wherein the at least one anti-clostridial agent is selected from the group consisting of: a vancomycin, a multi-valent polymer of vancomycin and a combination thereof.

5. The method of claim 1, wherein the opioid blocking agent is selected from the group consisting of: methyl naltrexone, naloxone hydrochloride and a combination thereof.

6. The method of claim 1, wherein the at least one anti-clostridial agent is vancomycin and the at least one opioid blocking agent is naloxone hydrochloride.

7. The method of claim 6, wherein 250 mg vancomycin is administered twice daily together with 10 mg naloxone hydrochloride.

8. The method of claim 1, wherein the at least one anti-clostridial agent and the at least one opioid blocking agent are administered simultaneously.

9. The method of claim 8, wherein the at least one anti-clostridial agent and the at least one opioid blocking agent are administered simultaneously in the form of a single composition.

10. The method of claim 1, wherein the at least one anti-clostridial agent and the at least one opioid blocking agent are administered separately.

11. The method of claim 1 wherein the at least one anti-clostridial agent or the at least one opioid blocking agent is administered orally in doses ranging from 0.01 mg per day to about 5000 mg per day.

12. The method of claim 1 wherein the at least one anti-clostridial agent or the at least one opioid blocking agent is administered orally in capsules or tablets.

13. The method of claim 1 wherein the at least one anti-clostridial agent or the at least one opioid blocking agent is administered in a single dosing regimen.

14. The method of claim 1 wherein the at least one anti-clostridial agent or the at least one opioid blocking agent is administered in enterically coated capsules or tablets.

15. The method of claim 1 wherein the at least one anti-clostridial agent or the at least one opioid blocking agent is administered in a divided dosing regimen.

* * * * *